United States Patent
Nishitani et al.

(10) Patent No.: US 8,450,557 B2
(45) Date of Patent: May 28, 2013

(54) TOP SHEET FOR ABSORBENT ARTICLE, PROCESS FOR ITS PRODUCTION AND ABSORBENT ARTICLE EMPLOYING THE SAME

(75) Inventors: Kazuya Nishitani, Kanonji (JP); Minako Sagisaka, Kanonji (JP); Kenji Oba, Kanonji (JP); Keijiro Yokoe, Kanonji (JP)

(73) Assignee: Unicharm Corporation (JP)

( * ) Notice: Subject to any disclaimer, the term of this patent is extended or adjusted under 35 U.S.C. 154(b) by 126 days.

(21) Appl. No.: 12/991,737

(22) PCT Filed: Apr. 9, 2009

(86) PCT No.: PCT/JP2009/057624
§ 371 (c)(1),
(2), (4) Date: Jan. 26, 2011

(87) PCT Pub. No.: WO2009/139259
PCT Pub. Date: Nov. 19, 2009

(65) Prior Publication Data
US 2011/0118691 A1    May 19, 2011

(30) Foreign Application Priority Data
May 15, 2008   (JP) .................... 2008-128741

(51) Int. Cl.
| *A61F 13/15* | (2006.01) |
| *B32B 3/00* | (2006.01) |
| *B32B 27/00* | (2006.01) |
| *A61F 13/511* | (2006.01) |
| *B32B 3/30* | (2006.01) |
| *B32B 27/12* | (2006.01) |
| *B32B 23/10* | (2006.01) |

(52) U.S. Cl.
CPC ............ *A61F 13/51104* (2013.01); *B32B 3/30* (2013.01); *B32B 27/12* (2013.01); *B32B 23/10* (2013.01)
USPC ........... 604/380; 604/378; 604/379; 428/198; 428/172; 428/156

(58) Field of Classification Search
USPC .................................. 604/378–380; 156/91
See application file for complete search history.

(56) References Cited

U.S. PATENT DOCUMENTS
3,945,386 A * 3/1976 Anczurowski et al. ....... 604/370
5,449,352 A * 9/1995 Nishino et al. ............... 604/383
(Continued)

FOREIGN PATENT DOCUMENTS
| EP | 0 792 629 | 9/1997 |
| EP | 2 034 066 | 3/2009 |

(Continued)

OTHER PUBLICATIONS

Extended European Search Report corresponding to EP09746466.3, dated Mar. 8, 2012.

*Primary Examiner* — Susan Su
(74) *Attorney, Agent, or Firm* — Lowe Hauptman Ham & Berner, LLP

(57) ABSTRACT

The top sheet for an absorbent article has a plurality of fused compressed sections, wherein the fused compressed sections are located on the lowermost side in the thickness direction of the top sheet, and the back side of the top sheet has recesses or low density regions having the lowest density within the top sheet, surrounding the fused compressed sections. The top sheet for an absorbent article having a plurality of fused compressed sections can be produced by a process wherein a top sheet is situated between a member with multiple protrusions and a member with multiple recesses that engage with the multiple protrusions, and the protrusions are pressed into the recesses.

11 Claims, 5 Drawing Sheets

U.S. PATENT DOCUMENTS

| | | | |
|---|---|---|---|
| 5,613,960 A * | 3/1997 | Mizutani | 604/365 |
| 5,932,316 A | 8/1999 | Cree et al. | |
| 6,013,349 A * | 1/2000 | Takeuchi et al. | 428/152 |
| 6,039,555 A * | 3/2000 | Tsuji et al. | 425/362 |
| 6,096,016 A * | 8/2000 | Tsuji et al. | 604/378 |
| 6,176,954 B1 * | 1/2001 | Tsuji et al. | 156/178 |
| 6,274,218 B1 * | 8/2001 | Shimizu | 428/137 |
| 6,660,902 B2 * | 12/2003 | Widlund et al. | 604/365 |
| 7,067,711 B2 | 6/2006 | Kuroda et al. | |
| 7,132,585 B2 * | 11/2006 | Kudo et al. | 604/380 |
| 7,267,860 B2 | 9/2007 | Toyoshima et al. | |
| 7,303,808 B2 * | 12/2007 | Taneichi et al. | 428/198 |
| 7,534,928 B2 * | 5/2009 | Sakamoto et al. | 604/378 |
| 7,674,949 B2 * | 3/2010 | Wahlstrom et al. | 604/380 |
| 7,994,386 B2 * | 8/2011 | Tokura et al. | 604/380 |
| 8,042,490 B2 * | 10/2011 | Takahashi et al. | 119/171 |
| 2003/0143376 A1 | 7/2003 | Toyoshima et al. | |
| 2004/0142151 A1 | 7/2004 | Toyoshima et al. | |
| 2006/0229579 A1 * | 10/2006 | Wahlstrom et al. | 604/366 |
| 2007/0093773 A1 * | 4/2007 | Tokura et al. | 604/385.101 |
| 2008/0119810 A1 * | 5/2008 | Kuroda et al. | 604/379 |
| 2009/0137977 A1 | 5/2009 | Fukae et al. | |

FOREIGN PATENT DOCUMENTS

| | | |
|---|---|---|
| JP | 09-234221 | 9/1997 |
| JP | 2000-262558 | 9/2000 |
| JP | 2004-181086 | 7/2004 |
| JP | 2005-145020 | 6/2005 |
| JP | 2006175689 A | 7/2006 |
| JP | 3868892 | 10/2006 |
| JP | 2008-025085 | 2/2008 |
| WO | 2004049995 A1 | 6/2004 |
| WO | WO 2007/043474 | 4/2007 |
| WO | WO 2008/146594 | 12/2008 |

* cited by examiner

Fig. 6
(A) 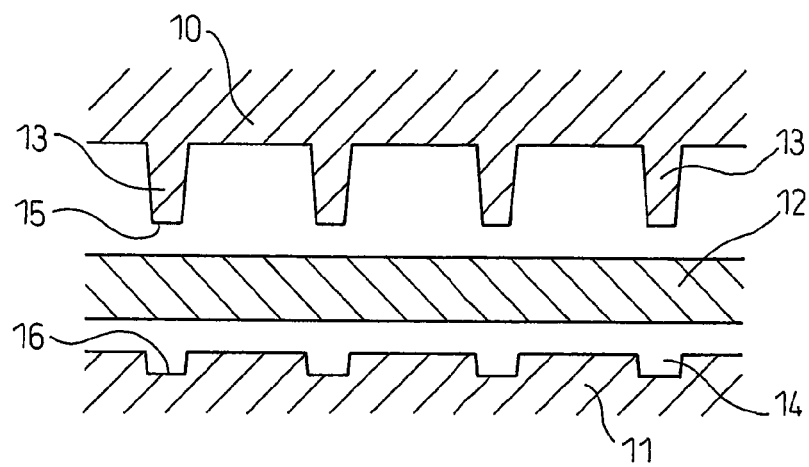
(B) 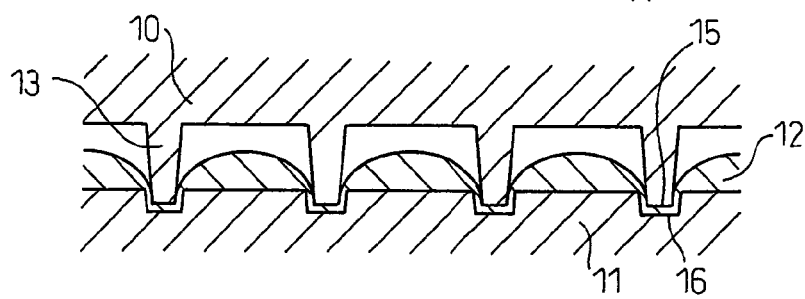
(C) 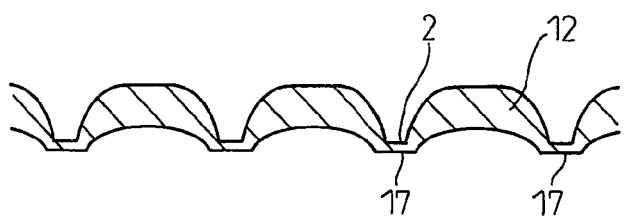
(D) 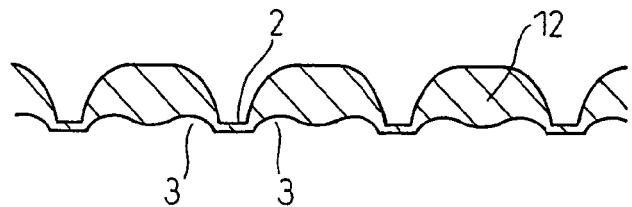

TOP SHEET FOR ABSORBENT ARTICLE, PROCESS FOR ITS PRODUCTION AND ABSORBENT ARTICLE EMPLOYING THE SAME

CROSS-REFERENCE TO RELATED APPLICATIONS

The present Application is based on International Application No. PCT/JP2009/057624, filed on Apr. 9, 2009, which in turn corresponds to Japanese Application No. 2008-128741, filed on May 15, 2008, and priority is hereby claimed under 35 USC §119 based on these applications. Each of these applications are hereby incorporated by reference in their entirety into the present application.

TECHNICAL FIELD

The present invention relates to a top sheet for absorbent articles such as sanitary napkins and disposable diapers, as well as to a process for its production and to absorbent articles employing the top sheet.

BACKGROUND ART

Japanese Patent No. 3868892 discloses a top sheet for absorbent articles, which is a nonwoven fabric having multiple heat-fused sections formed by embossing, wherein the fibers composing the nonwoven fabric between the heat-fused sections protrude in the direction of thickness of the nonwoven fabric, forming multiple elevated sections on the upper and lower sides. It further discloses that the nonwoven fabric has an upper layer and an adjacent lower layer, and discloses a production process wherein a lower layer containing at least 50 wt % latent crimping fiber is laminated with and an upper layer containing heat sealing fiber that either has essentially no heat shrinking property or undergoes no heat shrinkage at below the initial crimp temperature of the latent crimping fiber, and the laminate from the lower layer side is embossed to partially bond both webs by the multiple heat-fused sections to form a nonwoven fabric, after which the latent crimping fiber located around the heat-fused sections of the lower layer are pre-crimped and then the nonwoven fabric is heat treated at a temperature above the initial crimp temperature of the latent crimping fiber to shrink the lower layer, causing the upper layer and lower layer to protrude in the direction of thickness of the nonwoven fabric to form numerous elevated sections.

Japanese Unexamined Patent Publication No. 2004-181086 discloses an absorbent article wherein the top sheet comprises heat sealable fiber, a second layer containing heat sealable fiber is provided below the top sheet, the top sheet and second layer are compressed together and the top sheet and second layer fused together, and states that the absorbent article is produced by inserting the top sheet and second layer between heated rolls to form embossed sections, during which time a roll with a flat surface is placed against the surface of the second layer and an embossing roll on which protrusions have been formed in the surface is placed against the top sheet side (paragraph [0068]), and the cross-section of the article obtained in this manner shows a structure with irregularities on the front side and a flat rear side, wherein the fused sections where the top sheet and second layer have been fused are located at the lowermost section in the thickness direction (FIG. 4).

SUMMARY OF INVENTION

Technical Problem

The top sheet of the absorbent article described in Japanese Patent No. 3868892 has numerous elevated sections in the thickness direction of the nonwoven fabric, with respect to the heat-fused sections, and the heat-fused sections have the highest density within the top sheet while the elevated sections have lower density than the heat-fused sections. That is, a hill-valley structure is produced wherein the tops of the elevated sections have the lowest density and the density gradually increases toward the heat-fused sections. Fluids such as body fluids discharged from the body flow from the sparse density regions toward greater density regions by capillary action. Therefore, when a nonwoven fabric having such a structure is used as the top sheet of an absorbent article, fluid discharged from the body first permeates through the elevated sections and flows into the highest-density heat-fused sections due to the different density structure of the nonwoven fabric. However, since the elevated sections on the lower layer side, which protrude down in the thickness direction, have lower density than the heat-fused sections, it is extremely difficult for the fluid to migrate to the lower layer side. The body fluid therefore accumulates in the heat-fused sections, and during times of continuous discharge or large-volume discharge, the body fluid accumulates and diffuses extensively in the upper layer producing a sticky feel on the skin or the diffusion area widens raising the concern of leakage, while during times of large-volume discharge the fluid spreads over the surface resulting in actual leakage. During the production process as well, the fiber is restricted because it is essential for latent crimping fiber to be on the lower layer side, while the relatively high cost of latent crimping fiber increases overall cost; furthermore, because further heat treatment of the latent crimping fiber of the lower layer is necessary to shrink the fiber after the upper layer and lower layer have been layered and embossed, this enlarges and complicates the manufacturing line, and increases equipment cost.

Since the absorbent article having the construction shown in FIG. 4 of Japanese Unexamined Patent Publication No. 2004-181086 has the fused sections located on the lowermost side in the thickness direction, the fused sections are in contact with the absorber and fluid flowing into the fused sections migrates smoothly into the absorber so that the fluid does not accumulate in the fused sections. However, because the bottom sections of the non-fused sections are also in contact with the absorber, and the absorbent article is subject to pressure from the body, i.e., body pressure, with different positions or behaviors of the wearer, this results in pressure on the absorber and causes the fluid to be released from the absorber and flow back through the bottom section of the non-fused sections, thus widely staining the top sheet and either raising concern of leakage or producing actual leakage as a result of a large back flow volume.

Solution to Problem

The present invention provides a top sheet for an absorbent article having a plurality of fused compressed sections, wherein the fused compressed sections are located on the lowermost side in the thickness direction of the top sheet, and the back side of the top sheet has recesses or low density regions having the lowest density within the top sheet, surrounding the fused compressed sections.

Preferably, the fused compressed sections are located below the non-fused compressed sections in the thickness direction of the top sheet.

Preferably, the non-fused compressed sections form elevated sections that protrude out beyond the fused compressed sections on the front side of the top sheet, while side walls rising from the fused compressed sections toward the elevated sections are present around the perimeters of the fused compressed sections, the density being greatest in the order: elevated section center, side wall, fused compressed section.

Preferably, the density of the uppermost side in the thickness direction of the non-fused compressed section is lower than the density of the interior in the thickness direction of the non-fused compressed section.

Preferably, the top sheet is composed of two layers, a surface layer and a second layer.

The invention further provides a process for production of a top sheet for an absorbent article having a plurality of fused compressed sections, comprising the steps of situating a top sheet between a member with multiple protrusions and a member with multiple recesses that engage with the multiple protrusions, and pressing the protrusions into the recesses.

Preferably, in the process of the invention, the member with multiple protrusions and the member with multiple recesses are a pair of cooperating embossing rolls.

The invention provides an absorbent article comprising a top sheet, an absorber and a liquid-impermeable back sheet, wherein the absorber is situated between the top sheet and the back sheet and the fused compressed sections of the top sheet are situated in contact with the absorber.

Advantageous Effects of Invention

Since the fused compressed sections are situated on the lowermost side in the thickness direction in the top sheet for an absorbent article according to the invention, the fused compressed sections can contact with the absorber and fluids that permeate into the top sheet and flow into the fused compressed sections migrate smoothly into the absorber, while recesses or low density regions having the lowest density within the top sheet are present surrounding the fused compressed sections on the back side of the top sheet, and therefore fluids absorbed into the absorber when body pressure is applied to the absorbent article do not easily leak back through the bottom section of the non-fused compressed section.

BRIEF DESCRIPTION OF DRAWINGS

FIG. 6 is a cross-sectional view of a member with multiple protrusions and a member with multiple recesses, that can be used to produce a top sheet for an absorbent article according to the invention, and it shows an example of steps for production of a top sheet for an absorbent article according to the invention using the members.

DESCRIPTION OF EMBODIMENTS

Figure 1:
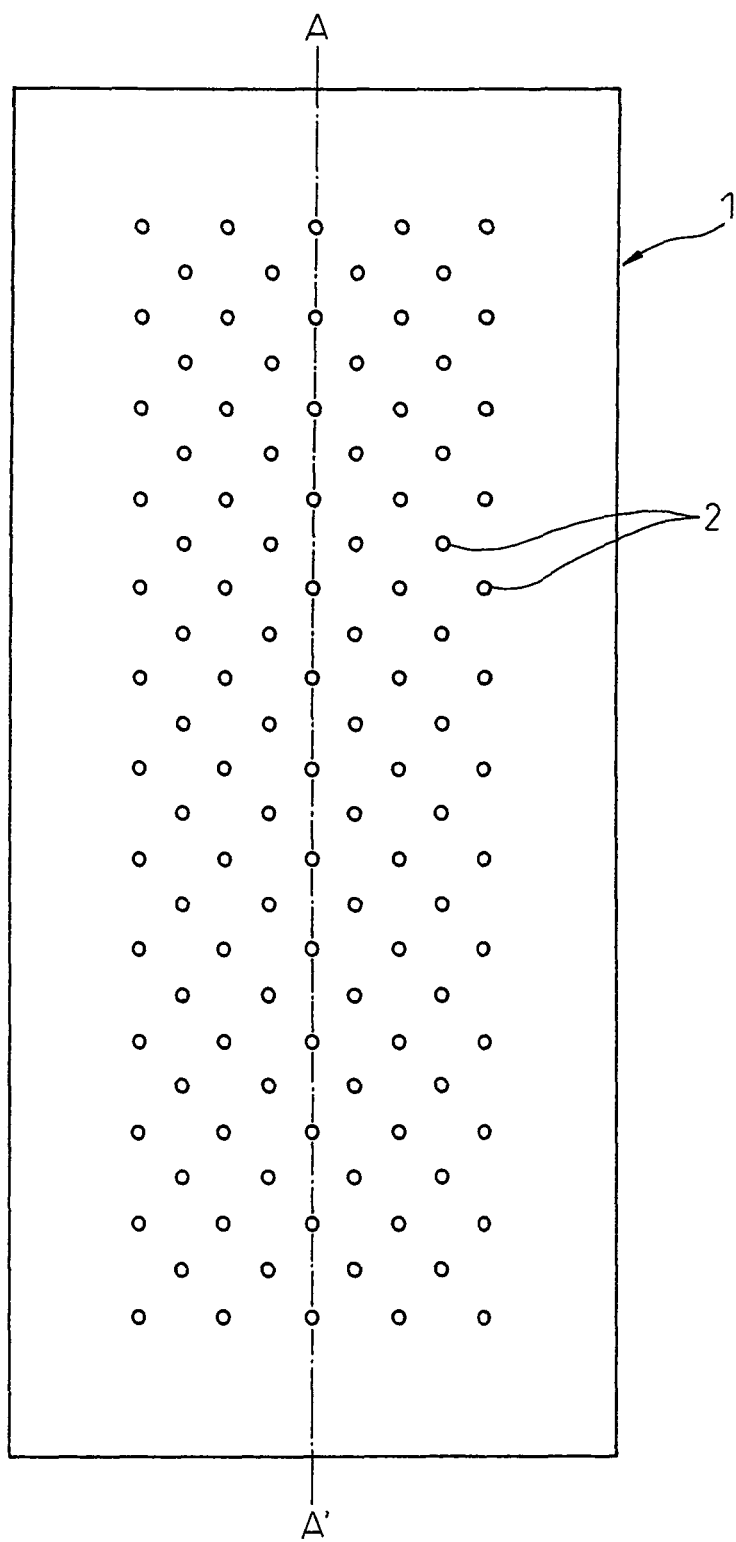
FIG. 1 is a plan view of an embodiment of a top sheet for an absorbent article according to the invention.

The invention will now be described in greater detail with reference to the accompanying drawings, with the understanding that the invention is not limited to the examples depicted in the drawings.

Figure 2:
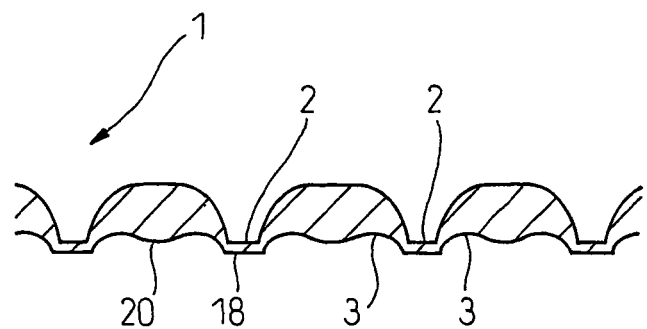
FIG. 2 is a cross-sectional view of an embodiment of a top sheet for an absorbent article according to the invention.

FIG. 1 is a plan view of one embodiment of a top sheet for an absorbent article according to the invention, and FIG. 2 is a partial cross-sectional view of the same along line A-A'. The top sheet 1 comprises a plurality of fused compressed sections 2, the fused compressed sections 2 being located on the lowermost side in the thickness direction of the top sheet 1, and the back side of the top sheet 1 having recesses 3 surrounding the fused compressed sections 2.

Figure 3:
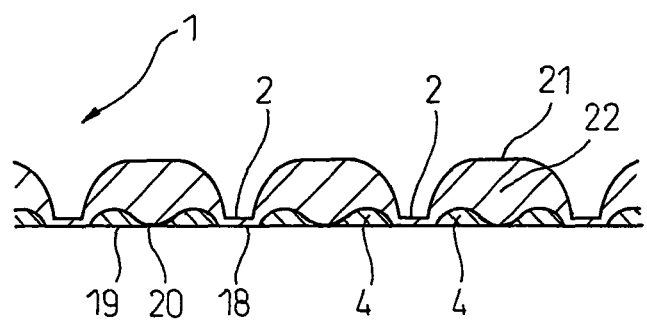
FIG. 3 is a cross-sectional view of another embodiment of a top sheet for an absorbent article according to the invention.

FIG. 3 is a cross-sectional view of a second embodiment of the top sheet for an absorbent article according to the invention. In this embodiment, the top sheet 1 is composed of a nonwoven fabric and the back side of the top sheet 1 has low density regions 4 having the lowest density within the top sheet, which surround the fused compressed sections 2.

Figure 4:
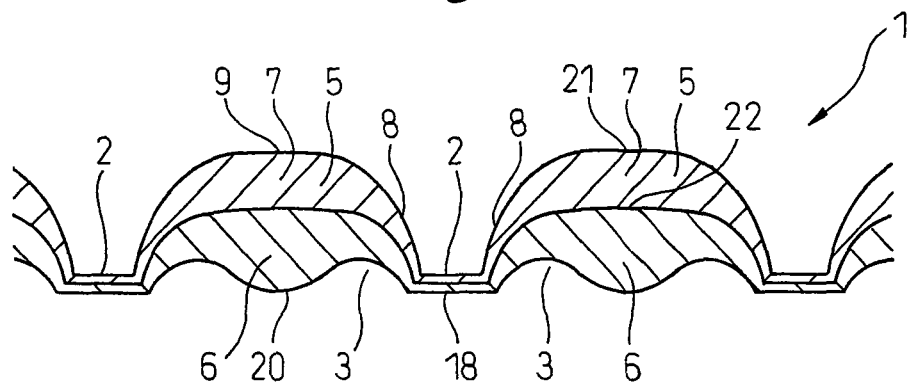
FIG. 4 is a cross-sectional view of yet another embodiment of a top sheet for an absorbent article according to the invention.

FIG. 4 is a cross-sectional view of a third embodiment of the top sheet for an absorbent article according to the invention. In this embodiment, the top sheet 1 comprises two layers, a surface layer 5 and a second layer 6, and the surface layer 5 and second layer 6 are each composed of nonwoven fabrics. The back side of the top sheet 1 has recesses 3 surrounding the fused compressed sections 2.

Figure 5:
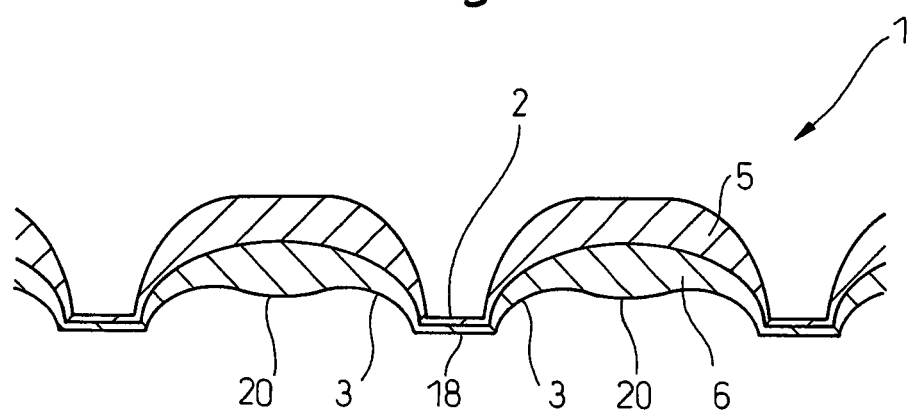
FIG. 5 is a cross-sectional view of yet another embodiment of a top sheet for an absorbent article according to the invention.

FIG. 5 is a cross-sectional view of a fourth embodiment of the top sheet for an absorbent article according to the invention. In this embodiment, the top sheet 1 comprises two layers, a surface layer 5 and a second layer 6, and the surface layer 5 and second layer 6 are each composed of nonwoven fabrics. Recesses 3 are present surrounding the fused compressed sections 2, and the fused compressed sections 2 are situated below the non-fused compressed sections in the thickness direction of the top sheet.

That the fused compressed sections are located on the lowermost side in the thickness direction of the top sheet 1 means that the sides of the non-fused compressed sections on the rear side of the top sheet do not protrude out from the rear side in the thickness direction past the plane 19 that contains the surface 18 of the fused compressed sections 2 on the rear side of the top sheet. To explain this with reference to the cross-sectional views in FIGS. 2 to 5, the lowermost sections 20 of the non-fused compressed sections on the back side of the top sheet are either in the same plane 19 as the plane 18 of the fused compressed sections 2 on the rear side of the top sheet (FIGS. 3 and 4), or are further toward the front side of the top sheet (FIGS. 2 and 5). That the lowermost sections 20 of the non-fused compressed sections on the back side of the top sheet are further toward the front side of the top sheet than the plane 19 that includes the plane 18 of the fused compressed sections 2 on the rear side of the top sheet, restated, means that the fused compressed sections 2 are situated lower in the thickness direction of the top sheet than the non-fused compressed sections, and examples of this situation are shown in FIG. 2 and FIG. 5. When the absorbent article is used as a sanitary napkin or disposable diaper, the front side of the top sheet is the side that contacts with the skin.

The structure of the top sheet for an absorbent article according to the invention will now be described in greater detail, with reference to FIG. 4. In the top sheet 1, the surface layer 5 and second layer 6 are layered and the surface layer 5 and second layer 6 are bonded by fused compressed sections 2. The top sheet 1 also has an irregular structure having the fused compressed sections 2 situated on the lowermost side in the thickness direction of the top sheet 1 and comprising elevated sections 7 rising toward the surface layer side, the elevated sections 7 being located between the fused compressed sections 2 and adjacent fused compressed sections 2, and the fused compressed sections 2 and elevated sections 7 alternating in a repeated fashion in the planar direction of the top sheet 1. The perimeters of the fused compressed sections 2, or the sections on both sides in the cross-sectional view, have side walls 8 that rise from the fused compressed sections 2 toward the elevated sections 7. The back side of the top sheet 1 has recesses 3 surrounding the fused compressed sections 2. The magnitude relationship for the relative density of the top sheet 1 is one wherein the side walls 8 are more dense than the peaks 9 of the elevated sections, and the fused compressed sections 2 are the highest-density sections within the top sheet 1, such that the density relationship is: peaks 9<side walls 8<fused compressed sections 2. The orientation of the fibers of the nonwoven fabric forming the surface layer 5 and second layer 6 is roughly parallel in the direction of the top sheet surface (the plane perpendicular to the direction of thickness) at the peaks 9 of the elevated sections 7, but the orientation of the nonwoven fabric fibers approaches the thickness direction from the peaks 9 of the elevated sections 7 toward the fused compressed sections 2 via the side walls 8.

The planar structure of the top sheet will now be explained. The arrangement of the fused compressed sections 2 on the top sheet 1 may be any desired pattern such as a zigzag, grid, linear or curved arrangement. The shapes of the fused compressed sections 2 may be any desired shapes such as circular, ellipsoid, square, rectangular, rhomboid, star-shaped or heart-shaped. The sizes of the fused compressed sections 2 are preferably 0.5 mm-15 mm, as the diameter when the fused compressed section 2 shapes are circular, the long axis when they are ellipsoid, the length of one side when they are square, and the long side when they are rectangular. At less than 0.5 mm, tearing may occur during working, or the bonding strength between the surface layer 5 and second layer 6 may not be adequately guaranteed, often resulting in peeling during use. At greater than 15 mm, on the other hand, the fused compressed sections 2 will be too large and hard, often producing an uncomfortable feel poorly suited for an absorbent article top sheet. The spacing between fused compressed sections 2 and their adjacent fused compressed sections 2 is preferably 2-20 mm. At less than 2 mm, the density of the elevated sections 7 between the fused compressed sections 2 and adjacent fused compressed sections 2 will become too high, thus interfering with smooth migration of fluids. At greater than 20 mm, the spacing will become too scattered and the bonding strength between the surface layer 5 and second layer 6 may not be adequately guaranteed, often resulting in peeling during use. The shapes of the fused compressed sections 2 and the spacing and arrangement between fused compressed sections 2 do not need to be the same throughout the top sheet 1, and any combination of different shapes and patterns may be employed within the range specified above.

The material composing the top sheet is preferably a nonwoven fabric, but this is not necessarily limitative. When the top sheet is composed of two layers, a surface layer and a second layer, the combination of materials for the surface layer and second layer may be selected from among nonwoven fabric/nonwoven fabric, porous plastic sheet/nonwoven fabric and nonwoven fabric/porous plastic sheet for the surface layer/second layer. As nonwoven fabrics there may be used fabrics produced from thermoplastic resins such as polyethylene, polypropylene or polyethylene terephthalate, using either these resins alone or producing core-sheath type, core-sheath eccentric type or side-by-side type composite synthetic fibers. In order to control the wettability of these nonwoven fabrics, a hydrophilic or water-repellent agent may be coated onto or incorporated into the fiber surface. The fibers may be heat sealed, hydroentangled, spunbond or the like, either alone or as mixed fibers to obtain the nonwoven fabric. From the viewpoint of hydrophilicity for body fluids, there may be included cellulose-based hydrophilic fibers such as pulp, chemical pulp, rayon, acetate or natural cotton. The fiber used is preferably 1.1-6.6 dtex and the basis weight is preferably adjusted to the range of 15-120 $g/m^2$. When the surface layer/second layer combination is nonwoven fabric/nonwoven fabric, the density of the nonwoven fabric of the second layer is preferably higher than the density of the nonwoven fabric of the surface layer, in consideration of fluid migration. That is, since fluids will tend to migrate toward the areas of higher density, a second layer with a higher density than the front layer is provided, thereby helping to promote absorption of fluid discharged from the body and prevent return of absorbed fluids. The surface layer or second layer may employ one layer each of the aforementioned materials, or they may be folded twice or three times for use as a two-layer or three-layer structure, or even 4 or more layers. A hot-melt adhesive may be used as appropriate between the surface layer and second layer.

The top sheet for an absorbent article according to the invention is formed in such a manner that the top sheet has multiple fused compressed sections, with elevated sections between the fused compressed sections and with the fused compressed sections situated on the lowermost side in the thickness direction of the top sheet, the perimeters of the fused compressed sections being surrounded by side walls that rise from the fused compressed sections toward the elevated sections, while the back side of the top sheet has recesses or low density regions with the lowest density within the top sheet, that surround the fused compressed sections. In this top sheet, the elevated sections are not compressed, and the sections of highest density are the fused compressed sections. The density of the top sheet increases from the elevated sections toward the fused compressed sections. When the top sheet having this structure is used as the top sheet of an absorbent article, the fused compressed sections which have the highest density are situated on the lowermost side in the thickness direction, and therefore contact with the absorber. Because of this structure, fluids discharged from the body first contact the elevated sections on the outer surface and begin to permeate, and then flow through the side walls into the fused compressed sections, following the density structure of the top sheet. Since the fused compressed sections are located on the lowermost side in the thickness direction of the top sheet and are in contact with the absorber, fluids flowing into the fused compressed sections migrate smoothly into the absorber so that the fluids do not accumulate in the fused compressed sections. In addition, the back side of the top sheet has recesses or low density regions having the lowest density within the top sheet, surrounding the fused compressed sections. Therefore, since fluid no longer migrates into other sections when it flows into the side walls, the fluid must necessarily collect only at the lowermost point of the top sheet, i.e. the fused compressed sections which are in contact with the absorber, thus allowing smooth and efficient transfer to the absorber and preventing spread of the fluid. Even when body fluid is repeatedly and continuously discharged, the fluid migrates smoothly from the elevated sections to the fused compressed sections and from the fused compressed sections to the absorber, similar to the initial absorption behavior, thus helping to reduce the diffusion area and complete absorption. Since the top sheet for an absorbent article according to the invention thus allows body fluid to smoothly migrate from the top sheet to the absorber without accumulating and spreading on the top sheet, the top sheet does not cause leakage or raise concern of leakage.

According to a preferred embodiment, the density of the uppermost sides 21 in the thickness direction of the non-fused compressed sections (that is, the peaks of the elevated sections) is lower than the density of the interiors 22 in the thickness direction of the non-fused compressed sections. When the top sheet is composed of two layers, a surface layer and a second layer, the density of the surface layer on the uppermost sides 21 in the thickness direction of the non-fused compressed sections is lower than the density of the surface layer at the interface with the second layer, directly below it. According to this embodiment, fluid discharged from the body first contacts and permeates the uppermost sides 21 in the thickness direction of the non-fused compressed sections, which are nearest to the skin, but then rapidly migrates into the interiors 22 which have higher density than the uppermost sides 21. The fluid that has permeated into the interiors 22 subsequently migrates toward the side walls, and then into the fused compressed sections. When the top sheet is composed of two layers, a surface layer and second layer, the second layer has the higher density, and therefore fluid that has permeated into the interiors 22 migrates into the second layer and then through the side walls to the fused compressed sections. According to this embodiment, therefore, fluid migrates rapidly from the surface to the interior, so that the fluid does not accumulate on the surface and a comfortable surface can be maintained, while an overall high fluid absorption rate is also obtained.

An absorbent article is usually subjected to pressure from the body (body pressure) due to different positions and behavior of the user, and therefore pressure is exerted on the absorber. This causes fluid to be released from the absorber, but since the absorber is usually composed mainly of a pulp layer, the pulp fibers are compressed together by the pressure releasing the fluid held between the pulp fibers, such that the top sheet becomes wetted by reverse flow which diffusely contaminates the top sheet, raising the concern of leakage, or in the case of a large reverse flow volume, the reverse flowing fluid may stick to the skin or may leak from the sides or rear. With the top sheet of the invention, however, even when body pressure is applied to the absorbent article after the absorber has absorbed body fluid, the spaces (sections corresponding to recesses) or low density regions between the absorber and the top sheet prevent body fluid release from the absorber from flowing back to the front side of the top sheet. Furthermore, although the fused compressed sections are in contact with the absorber, a density gradient in the order (fused compressed sections>side walls>elevated sections) exists which slows migration of fluid from the absorber through the fused compressed sections to the skin side of the top sheet. Therefore, the fear of leakage and leakage itself can be reduced, not only because body fluids can smoothly migrate from the surface layer to the second layer and from the second layer to the absorber without accumulating and spreading on the top sheet, but also because fluid that has been absorbed into the absorber does not return back and spread in the top sheet. The effect of preventing reverse flow of fluid from the absorber back to the top sheet when body pressure is applied is greater when recesses are present, i.e. when spaces exist between the absorber and the top sheet, than when the low density regions are present around the fused compressed sections, because body fluid released from the absorber can accumulate within the spaces.

The top sheet for an absorbent article according to the invention can be produced by situating a top sheet between a member with multiple protrusions and a member with multiple recesses that engage with the multiple protrusions, and pressing the protrusions into the recesses.

FIG. 6 is a cross-sectional view of a member 10 with multiple protrusions and a member 11 with multiple recesses, that can be used to produce a top sheet for an absorbent article according to the invention, and it shows an example of steps for production of a top sheet for an absorbent article according to the invention using the members. The member 10 with multiple protrusions and the member 11 with multiple recesses are preferably a pair of cooperating embossing rolls, where the protrusions 13 formed on one of the embossing rolls engage with the recesses 14 of the other embossing roll. FIG. 6(A) shows the state before the protrusions 13 of the member 10 with multiple protrusions have been pressed into the recesses 14 of the member 11 with multiple recesses, and FIG. 6(B) shows the state where the protrusions 13 of the member 10 with multiple protrusions have been pressed into the recesses 14 of the member 11 with multiple recesses. FIG. 6(C) is a cross-sectional view of the top sheet that has passed through the embossing rolls and is subjected to conveyance tension. FIG. 6(D) shows a cross-sectional view of the top sheet after it has been released from the conveyance tension.

The top sheet 12 is conveyed on the line in a state of tension while being inserted between the member 10 with multiple protrusions and the member 11 with multiple recesses. When the top sheet 12 is composed of two layers, a surface layer and a second layer, it is inserted in such a manner that the surface layer contacts with the member 10 with multiple protrusions while the second layer contacts with the member 11 with multiple recesses. The member 10 with multiple protrusions and the member 11 with multiple recesses are heated to a temperature that allows sufficient softening of the top sheet 12 (or both the surface layer and second layer, when it is composed of two layers). When the protrusions 13 of the member 10 with multiple protrusions are pressed into the recesses 14 of the member 11 with multiple recesses, the protrusions 13 deform the top sheet 12 while indenting the recesses 14, and when the tips 15 of the protrusions 13 meet the bottom sections 16 of the recesses 14, the temperature and pressure on the top sheet 12 increases causing fusion so that fused compressed sections 2 with protrusions 17 are formed even further below the original lowermost side of the top sheet 12, as shown in FIG. 6(B). The top sheet 12 that has passed through the indenting step is subjected to tension in the line conveyance direction and therefore has the cross-sectional shape shown in FIG. 6(C), but when the top sheet 12 leaves the manufacturing line and is released from the conveyance tension, recesses 3 or low density regions are formed surrounding the fused compressed sections 2, as shown in FIG. 6(D).

According to the process of the invention, the uppermost side in the thickness direction of the top sheet is stretched to a greater extent than the interior in the thickness direction of the top sheet by the tension of the indenting step, and therefore when the top sheet is composed of a nonwoven fabric, the fibers of the nonwoven fabric are pulled apart in the direction of stretching such that after the indenting step, the density of the uppermost side 21 in the thickness direction of the non-fused compressed sections of the top sheet is lower than the density of the interior 22 in the thickness direction of the non-fused compressed sections.

The depths of the recesses of the member with multiple recesses is preferably 0.5-3.5 mm and more preferably 1.0-3.0 mm. If the depths of the recesses are too shallow, the fused compressed sections of the obtained top sheet will be higher (more toward the front side of the top sheet) than the lowermost side in the thickness direction of the top sheet. Conversely, if the depths of the recesses are too deep the perimeters of the fused compressed sections may break apart.

The heights of the protrusions of the member with multiple protrusions are greater than the depths of the recesses of the member with multiple recesses, preferably at least by the thickness of the top sheet before working. For example, the heights of the protrusions are preferably 1-5 mm larger and more preferably 1.2-3.0 mm larger than the depths of the recesses. If the heights of the protrusions are too low, sections other than the fused compressed sections will be compressed. Conversely, if the heights of the protrusions are too high it will be difficult to apply adequate pressure during indenting.

The spacing (clearance) between the member with multiple protrusions and the member with multiple recesses when they meet during the indenting is preferably 0.0-0.1 mm and more preferably 0.0-0.05 mm. If the clearance is too large it will not be possible to accomplish fused compression.

The preferred temperature for the member with multiple protrusions and the member with multiple recesses will differ depending on the material composing the top sheet. When the top sheet is composed of a nonwoven fabric, the temperature is preferably 105-140° C. and more preferably 115-130° C. If the temperature is too low it will not be possible to accomplish fusion. If the temperature is too high, on the other hand, the sheet will become hard or will melt, resulting in open holes. When the top sheet is composed of a polyethylene net, the temperature is preferably 60-90° C. and more preferably 70-80° C. If the temperature is too low it will not be possible to accomplish fusion. If the temperature is too high, on the other hand, the sheet will melt resulting in open holes.

The pressure during the indenting step is preferably 160-700 MPa and more preferably 250-520 MPa. If the pressure is too low, it will not be possible to sufficiently accomplish fused compression. If the pressure is too high, on the other hand, the embossing roll may break.

The member with multiple protrusions and the member with multiple recesses used for production of the top sheet of the invention may both be rolls, with fused compression being accomplished using a rotor, or they may be plates with fused compression being accomplished by sandwiching between them. The method for fused compression may be a method in which the member with multiple protrusions and the member with multiple recesses are heated at a temperature sufficient to adequately soften the top sheet, or a method in which fused compression is accomplished by ultrasonic bonding.

When the top sheet is composed of two layers, a surface layer and a second layer, it will be possible, in a single step, to bond the surface layer and second layer while simultaneously obtaining a top sheet wherein the fused compressed sections are situated on the lowermost side in the thickness direction of the top sheet. Furthermore, since it is possible to obtain a top sheet for an absorbent article having an irregular surface structure by working two sheets for any surface layer and second layer in a single working step, there is no restriction to expensive materials and cost can thus be reduced, while the manufacturing line is more compact and simplified and equipment cost can be minimized as a result.

EXAMPLES

Example 1

After blending a 2.6-dtex core-in-sheath fiber having a core of poly(ethylene terephthalate) and a sheath of polyethylene, a 2.2-dtex core-in-sheath fiber having a core of poly(ethylene terephthalate) and a sheath of polyethylene, and a 3.3-dtex core-in-sheath fiber having a core of polypropylene and a sheath of polyethylene, the blend was prepared to a total of 30 g/m$^2$ and used in an air-through method to obtain a nonwoven fabric which was used as a surface layer, while a 2.2-dtex core-in-sheath fiber having a core of polypropylene and a sheath of polyethylene and a 3.3-dtex core-in-sheath fiber having a core of polypropylene and a sheath of polyethylene were blended, prepared to a total of 38 g/m$^2$ and used in an air-through method to obtain a nonwoven fabric which was used as a second layer, coating a hot-melt adhesive between the surface layer and second layer to 10 g/m$^2$, at a width of 1.0 mm and a pitch of 2.0 mm.

A metal roll having cylindrical protrusions with 1.4 mm-diameter circular-shaped tips and heights of 2.8 mm arranged in a zigzag fashion on the peripheral surface at a pitch of 6.0 mm in the machine direction (MD) and transverse direction (CD) (this will hereinafter be referred to as "protrusion-formed metal roll") was used as a member with multiple protrusions, while a metal roll capable of pairing and engaging with the protrusion-formed metal roll, and having recesses with depths of 1.4 mm and slightly larger diameters than the cylindrical protrusions of the protrusion-formed metal roll, located at positions corresponding to the cylindrical protrusions on the protrusion-formed metal roll during engagement with the protrusion-formed metal roll, was used as a member with multiple recesses (this will hereinafter be referred to as "recess-formed metal roll"). The laminated body obtained by attaching the surface layer and the second layer with the hot-melt adhesive was inserted between the protrusion-formed metal roll and the recess-formed metal roll and a pressure of 250 MPa was applied to form fused compressed sections. The temperatures of the protrusion-formed metal roll and the recess-formed metal roll were both raised to 125° C., and the clearance was set to 0.0 mm between the tips of the protrusions and the bottoms of the recesses.

Figure 7:
FIG. 7 is a photomicrograph of a cross-section of a top sheet for an absorbent article, obtained as an example of the invention.
Figure 8:
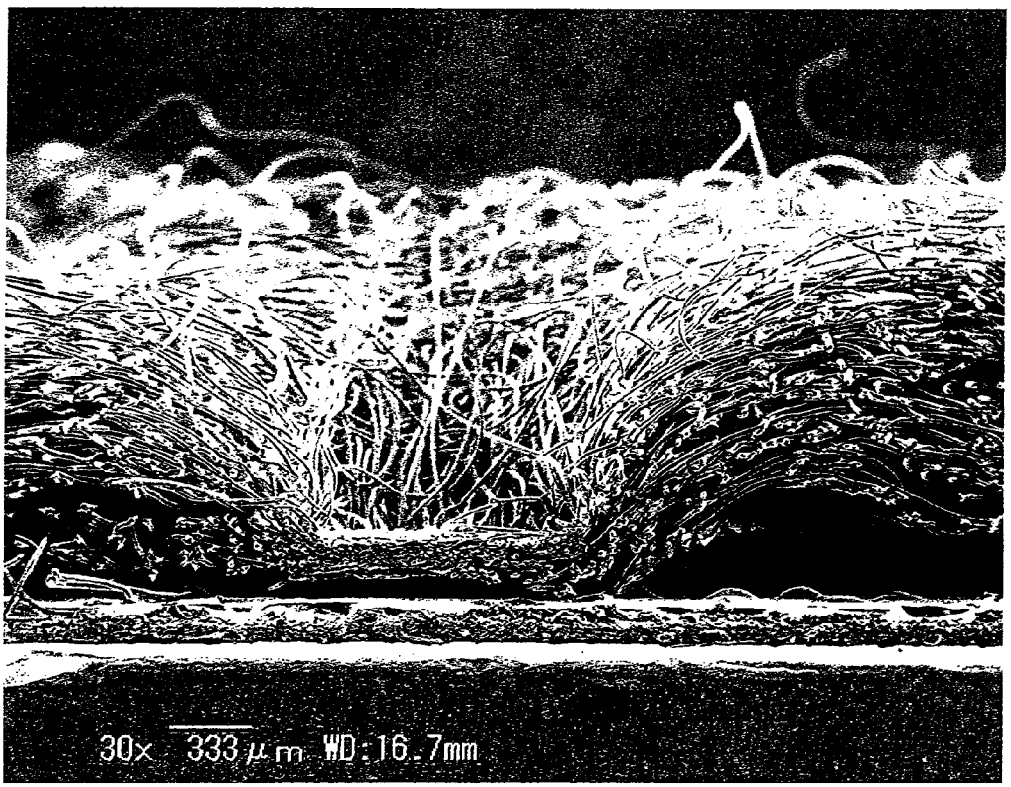
FIG. 8 is a photomicrograph of a cross-section of a top sheet for an absorbent article, obtained as Example 1 of the invention.

This procedure yielded a top sheet with multiple 1.4-mmφ circular fused compressed sections arranged in a zigzag fashion at a pitch of 6 mm in the MD direction and CD direction of each of the fused compressed sections. The obtained top sheet was cut in the MD direction (line A-A' in FIG. 1) and the cross-section was observed with a microscope. Photomicrographs thereof are shown in FIG. 7 and FIG. 8.

An absorber and a back sheet were laminated on the obtained top sheet to produce a sanitary napkin with a dimension of 25 cm in the lengthwise direction. The sanitary napkin was provided for diffusion evaluation. For the diffusion evaluation, 6 mL of artificial menstrual blood (viscosity in the range of 22-26 mPa·s) was dropped at a rate of 15 mL/min, the length of the diffusion region of the artificial menstrual blood was measured in the longitudinal direction (MD) and transverse direction (CD), and the rectangular area of their product was calculated to obtain the diffusion area. The average value for the diffusion areas obtained for 36 samples was 694 cm$^2$, the minimum diffusion area was 428 cm$^2$ and the maximum diffusion area was 868 cm$^2$.

The sanitary napkin was then evaluated for surface quick-drying property. For the surface quick-drying evaluation, 6 mL of artificial menstrual blood was dropped at a rate of 95 mL/min onto the skin-contacting side of the sanitary napkin, and then a KES-F7 Finger Robot Thermo-Lab by Kato Tech Corp. was used to measure the Qmax (heat transfer rate) at the dropping location of the surface of the sanitary napkin after 1 minute, 3 minutes, 5 minutes and 7 minutes. A larger Qmax value corresponds to a greater feeling of dampness. The average values for the Qmax values obtained for three samples were 0.208 after 1 minute, 0.150 after 3 minutes, 0.118 after 5 minutes and 0.097 after 7 minutes.

Comparative Example 1

Figure 9:
FIG. 9 is a photomicrograph of a cross-section of a top sheet for an absorbent article, obtained as Comparative Example 1 of the invention.

A top sheet with multiple fused compressed sections was obtained in the same manner as the previous example, except that an ordinary flat metal roll without recesses was used instead of the recess-formed metal roll. The obtained top sheet was cut in the MD direction and the cross-section was observed with a microscope. A photomicrograph thereof is shown in FIG. 9. The photomicrograph shows that the fused compressed sections of the top sheet of the comparative example are not positioned on the lowermost side in the thickness direction of the top sheet.

An absorber and a back sheet were laminated on the obtained top sheet to produce a sanitary napkin with a dimension of 25 cm in the lengthwise direction. When the sanitary napkin was subjected to diffusion evaluation in the same manner as the example, the average value for the diffusion area was 1440 cm$^2$, the minimum diffusion area was 1190 cm$^2$ and the maximum diffusion area was 1771 cm$^2$, and therefore spread of the menstrual blood in the plane was greater than in the example.

The sanitary napkin was then evaluated for surface quick-drying property in the same manner as the example. The average values for the Qmax values obtained for three samples were 0.257 after 1 minute, 0.191 after 3 minutes, 0.174 after 5 minutes and 0.148 after 7 minutes, and therefore the surface quick-drying property was inferior to the example.

Industrial Applicability

The top sheet absorbent article of the invention can be used as a top sheet for an absorbent article such as a sanitary napkin and disposable diaper.

Reference Signs List
1 Top sheet
2 Fused compressed section
3 Recess
4 Low density region
5 Surface layer
6 Second layer
7 Elevated section
8 Side wall
9 Peak of elevated section
10 Member with multiple protrusions
11 Member with multiple recesses
12 Top sheet
13 Protrusion
14 Recess
15 Tip of protrusion
16 Bottom of recess
17 Protrusion
18 Surface of top sheet rear side of fused compressed section
19 Plane containing surface of top sheet rear side of fused compressed section
20 Lowermost section of top sheet rear side of non-fused compressed section
21 Uppermost side in thickness direction of non-fused compressed section
22 Interior in thickness direction of non-fused compressed section

The invention claimed is:

1. A top sheet for an absorbent article, the top sheet comprising:
   a plurality of fused compressed sections; and
   a plurality of non-fused compressed sections alternately arranged with respect to the plurality of fused compressed sections,
   wherein
   the non-fused compressed sections have uppermost sections, lowermost sections opposite to the uppermost sections in a thickness direction of the top sheet, and recesses adjacent to the lowermost sections,
   the lowermost sections are convex away from the corresponding uppermost sections to define the recesses, and
   the fused compressed sections are located on a lowermost side of the top sheet in the thickness direction.

2. A top sheet according to claim 1, wherein the fused compressed sections are located lower than the lowermost sections of the non-fused compressed sections in the thickness direction of the top sheet.

3. A top sheet according to claim 1, wherein the non-fused compressed sections further comprise
   elevated sections at the uppermost sections, the elevated sections protruding upwardly and beyond the fused compressed sections in the thickness direction, and
   side walls rising from the fused compressed sections toward the elevated sections and surrounding perimeters of the fused compressed sections, and
   wherein
   the elevated sections have elevated section centers, and
   a density of the top sheet increases in the order: the elevated section centers, the side walls, the fused compressed sections.

4. A top sheet according to claim 1, wherein
   the non-fused compressed sections further comprise intermediate sections between the uppermost sections and the lowermost sections in the thickness direction, and
   a density of the top sheet in each of the uppermost sections is lower than in the corresponding intermediate section.

5. A top sheet according to claim 1, wherein the top sheet comprises a surface layer and a second layer.

6. A top sheet according to claim 5, wherein the surface layer and the second layer comprise the plurality of non-fused compressed sections and the plurality of fused compressed sections,
   the plurality of non-fused compressed sections at the second layer includes the lowermost sections, and
   the plurality of non-fused compressed sections at the surface layer is free of the lowermost sections.

7. A top sheet according to claim 1, further comprising low density regions provided at the recesses and adjacent to the fused compressed sections.

8. A top sheet according to claim 1, wherein, as viewed in a cross-section of the top sheet, each of the lowermost sections defines two recesses of the corresponding non-fused compressed section.

9. An absorbent article, comprising:
a top sheet according to claim 1,
an absorber, and
a liquid-impermeable back sheet,
wherein the absorber is situated between the top sheet and the back sheet, and the fused compressed sections of the top sheet contact the absorber.

10. A top sheet for an absorbent article, the top sheet comprising:
a plurality of fused compressed sections;
a plurality of non-fused compressed sections alternately arranged with respect to the plurality of fused compressed sections; and
low density regions surrounding the plurality of fused compressed sections and below the plurality of non-fused compressed sections,
wherein
the non-fused compressed sections have uppermost sections, lowermost sections opposite to the uppermost sections in a thickness direction of the top sheet, and recesses adjacent to the lowermost sections,
surfaces of the recesses are located higher than surfaces of the lowermost sections in the thickness direction, and
a density of the top sheet in the low density regions is lower than in the lowermost sections.

11. A top sheet according to claim 10, wherein the lowermost sections are convex away from the corresponding uppermost sections to define the recesses.

\* \* \* \* \*